US00PP14636P29

(12) United States Plant Patent
Verwer

(10) Patent No.: US PP14,636 P2
(45) Date of Patent: Mar. 23, 2004

(54) DAHLIA PLANT NAMED 'KARMA BON BINI'

(50) Latin Name: *Dahlia hybrida*
Varietal Denomination: Karma Bon Bini

(75) Inventor: Aad W. M. Verwer, Lisse (NL)

(73) Assignee: Verwer Dahlias B.V., Lisse (NL)

( * ) Notice: Subject to any disclaimer, the term of this patent is extended or adjusted under 35 U.S.C. 154(b) by 0 days.

(21) Appl. No.: 10/437,950

(22) Filed: May 13, 2003

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—C. A. Whealy

(57) ABSTRACT

A distinct cultivar of Dahlia plant named 'Karma Bon Bini', characterized by its straight and strong flowering stems; freely basal branching growth habit; cactus-type inflorescence form; yellow and red bi-colored ray florets; excellent garden performance; and excellent inflorescence longevity.

2 Drawing Sheets

Botanical classification/cultivar designation: *Dahlia hybrida* cultivar Karma Bon Bini.

BACKGROUND OF THE INVENTION

The present Invention relates to a new and distinct cultivar of Dahlia plant, botanically known as *Dahlia hybrida* and hereinafter referred to by the name 'Karma Bon Bini'.

The new Dahlia is a product of a planned breeding program conducted by the Inventor in Lisse, The Netherlands. The objective of the breeding program is to create new cut flower Dahlia cultivars with straight strong flowering stems, decorative inflorescence form, attractive ray floret colors, and good inflorescence longevity.

The new Dahlia originated from a cross-pollination made by the Inventor in 1996 of the *Dahlia hybrida* cultivar Bridgeview Aloha, not patented, as the female or seed parent with an unidentified selection of *Dahlia hybrida*, not patented, as the male or pollen parent. The new Dahlia was discovered and selected by the Inventor as a single flowering plant within the progeny of the stated cross-pollination grown in a controlled environment in Lisse, The Netherlands, in the summer of 1997. The selection of this plant was based on its strong straight stems and attractive ray floret coloration.

Asexual reproduction of the new Dahlia by cuttings was first conducted in a controlled environment in Lisse, The Netherlands in the Spring of 1998. Asexual reproduction by cuttings has shown that the unique features of this new Dahlia are stable and reproduced true to type in successive generations.

SUMMARY OF THE INVENTION

The cultivar Karma Bon Bini has not been observed under all possible environmental conditions. The phenotype may vary somewhat with variations in environment such as temperature, daylength and light intensity without, however, any variance in genotype.

The following traits have been repeatedly observed and are determined to be the unique characteristics of 'Karma Bon Bini'. These characteristics in combination distinguish 'Karma Bon Bini' as a new and distinct Dahlia cultivar:

1. Straight and strong flowering stems.
2. Freely basal branching growth habit.
3. Cactus-type inflorescence form.
4. Yellow and red bi-colored ray florets.
5. Excellent garden performance.
6. Excellent inflorescence longevity.

Plants of the new Dahlia are most similar to plants of the female parent, the cultivar Bridgeview Aloha. However, in side-by-side comparisons conducted in Lisse, The Netherlands, plants of the new Dahlia differed from plants of the cultivar Bridgeview Aloha in the following characteristics:

1. Plants of the new Dahlia were shorter than plants of the cultivar Bridgeview Aloha.
2. Plants of the new Dahlia had stronger flowering stems than plants of the cultivar Bridgeview Aloha.
3. Plants of the new Dahlia had cactus-type inflorescences whereas plants of the cultivar Bridgeview Aloha had decorative-type inflorescences.
4. Ray floret coloration of plants of the new Dahlia was stronger and resisted fading better than plants of the cultivar Bridgeview Aloha.

Plants of the new Dahlia differ primarily from plants of the male parent, an unidentified selection, in ray floret coloration.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph on the first sheet comprises a side perspective view of a typical flowering stem of 'Karma Bon Bini'.

The photograph on the second sheet is a close-up view of typical inflorescences of 'Karma Bon Bini'.

DETAILED BOTANICAL DESCRIPTION

In the following description, color references are made to The Royal Horticultural Society Colour Chart, 1995 Edition, except where general terms of ordinary dictionary significance are used. The aforementioned photographs and the following observations and measurements describe plants grown and flowered during the summer and early autumn in Lisse, The Netherlands, in an outdoor nursery and under conditions which approximate those generally used in commercial production. During the production of the plants, day temperatures ranged between 15 and 30° C. and night temperatures ranged between 14 and 20° C. Plants were pinched one time about three to four weeks after planting rooted cuttings. Plants were about four months old when the photographs and the description were taken.

Botanical classification: *Dahlia hybrida* cultivar Karma Bon Bini.

Parentage:

*Female, or seed, parent.*—*Dahlia hybrida* cultivar Bridgeview Aloha, not patented.

*Male, or pollen, parent.*—Unidentified selection of *Dahlia hybrida*, not patented.

Propagation:

*Type.*—By vegetative cuttings.

*Time to initiate roots.*—Summer: About 10 days at 18° C. Winter: About 12 days at 18° C.

*Time to produce a rooted young plant.*—Summer: About 24 days at 18° C. Winter: About 27 days at 18 to 20° C.

*Root description.*—Fine, fibrous and well-branched; older roots, fleshy.

*Tuber description.*—Shape: Fusiform. Clump diameter: About 25 cm. Color: Close to 199C.

Plant description:

*Appearance.*—Perennial cactus-type inflorescence cut Dahlia. Straight and strong flowering stems; inverted triangle; moderately vigorous.

*Plant height.*—About 120 cm.

*Plant diameter.*—About 35 cm.

*Flowering stem description.*—Quantity of flowering stems per plant: Pinched plants will produce about 10 to 12 flowering stems. Length: About 80 cm. Diameter: Towards base: About 2.3 cm. Towards apex: About 3 mm. Internode length: About 8 to 18 cm. Strength: Strong. Aspect: Erect, straight. Texture: Glabrous, smooth. Color: Towards base, 146C; towards apex, 146C overlain with anthocyanin, close to 177A.

*Foliage description.*—Arangement: Leaves opposite; leaves may be simple or compound with three or five leaflets. Shape: Ovate. Apex: Acute. Base: Attenuate. Margin: Serrate. Length: Simple leaves: About 11 cm. Compound leaves with three leaflets: About 19 cm. Compound leaves with five leaflets: About 25 cm. Width: Single leaves: About 5.5 cm. Compound leaves with three leaflets: About 10 cm. Compound leaves with five leaflets: About 13 cm. Venation pattern: Pinnate. Texture: Smooth, glabrous; leathery. Color: Developing foliage, upper surface: 137A. Developing foliage, lower surface: 191A. Fully developed foliage, upper surface: 137A to darker than 137A. Fully developed foliage, lower surface: 191A. Venation, upper surface: 138B. Venation, lower surface: 144A. Petioles: Length: About 3 cm. Diameter: About 1.4 mm. Texture, upper and lower surfaces: Smooth, glabrous. Color, upper surface: 146C. Color, lower surface: 146D.

Inflorescence description:

*Appearance.*—Cactus-type inflorescence form. Inflorescences borne on terminals, arising from leaf axils. Ray and disc florets develop acropetally on the receptacle. Inflorescences not fragrant. Inflorescences persistent.

*Flowering response.*—Flowering recurrent to continuous during the summer and autumn in The Netherlands.

*Postproduction longevity.*—On the plant, inflorescences maintain good color and substance for about 23 days in an outdoor environment. As cut flowers, inflorescences maintain good color and substance for about 8 to 12 days in an indoor environment.

*Quantity of inflorescences per flowering stem.*—One per lateral stem; about seven inflorescences per flowering stem; about 70 inflorescences per plant develop during the growing season.

*Inflorescence size.*—Shape, in profile: Roughly hemispherical. Diameter: About 13 cm. Depth (height): About 9.5 cm. Diameter of disc: About 4.5 cm; inconspicuous. Receptacle diameter: About 3.5 cm. Receptacle height: About 2.1 mm.

*Inflorescence buds* (*just before opening*).—Length: About 1.8 cm. Diameter: About 2.4 cm. Shape: Oblate. Color: 151A.

*Ray florets.*—Length, fully developed: About 6.4 cm. Width, fully developed: About 2.1 cm. Shape: Elongated oblong. Apex: Acute. Base: Attenuate. Margin: Entire. Texture: Smooth, glabrous; shiny. Number of ray florets per inflorescence: About 147 arranged in about 21 rows. Venation pattern: Parallel. Color: When opening, upper surface: Towards base, 1A; mid-section, 44A; towards apex, between 45A and 46A. When opening, lower surface: Towards base, 1B; towards apex, 46A. Fully opened, upper surface: Towards base, 2A; mid-section, blend of 2A and 45A; towards apex, 45A. Fully opened, lower surface: 2B; towards the apex, 2B blended with 43B.

*Disc florets.*—Number of disc florets per inflorescence: About 37. Shape: Tubular, elongated. Apex: Five-pointed. Base: Attenuate. Length: About 1.6 cm. Diameter, apex: About 2 mm. Diameter, base: About 3 mm. Color: Immature: 2C. Mature: Apex: 21A. Mid-section: 4A. Base: 2C.

*Phyllaries.*—Quantity: One whorl with about 5 to 6 phyllaries. Shape: Ovate. Apex: Acute. Base: Attenuate. Margin: Entire. Length: About 1 cm. Width: About 4.6 mm. Texture, upper and lower surfaces: Smooth, glabrous. Color, upper surface: 146B. Color, lower surface: 146A.

*Peduncles.*—Length, terminal peduncle: About 28 cm. Length, fourth peduncle: About 22 cm. Length, seventh peduncle: About 22 cm. Diameter: About 2.4 mm. Strength: Strong. Texture: Smooth, glabrous. Color: 146C; towards the apex, 146C overlain with close to 177A.

*Reproductive organs.*—Androecium: Present on disc florets only. Stamen quantity: About five per floret. Anther length: About 4 mm. Anther color: 21B. Pollen amount: Scarce. Pollen color: 17A. Gynoecium: Present on ray and disc florets. Pistil quantity: One per floret. Pistil length: About 5 mm. Stigma color: 24A. Style length: About 3 mm. Style color: 150C. Ovary color: 2D.

*Seeds/fruits.*—Seed and fruit development has not been observed.

Disease/pest resistance: Resistance to pathogens and pests common to Dahlias has not been observed on plants grown under commercial greenhouse or outdoor conditions.

Weather tolerance: Plants of the new Dahlia have been observed to be very tolerant to wind, rain and full sun conditions. Plants of the new Dahlia have been observed to be tolerant temperatures from 0 to 40° C.

It is claimed:

1. A new and distinct cultivar of Dahlia plant named 'Karma Bon Bini', as illustrated and described.

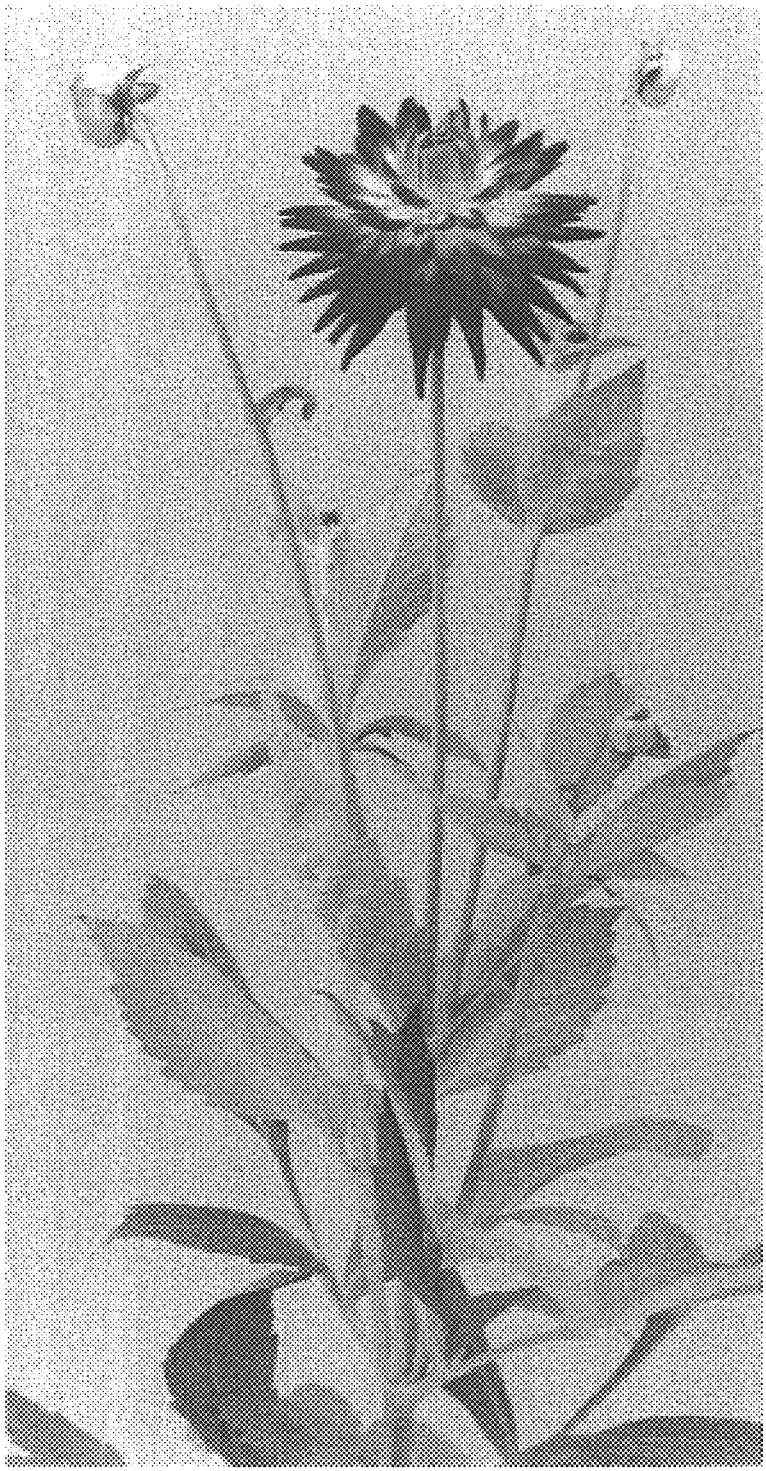

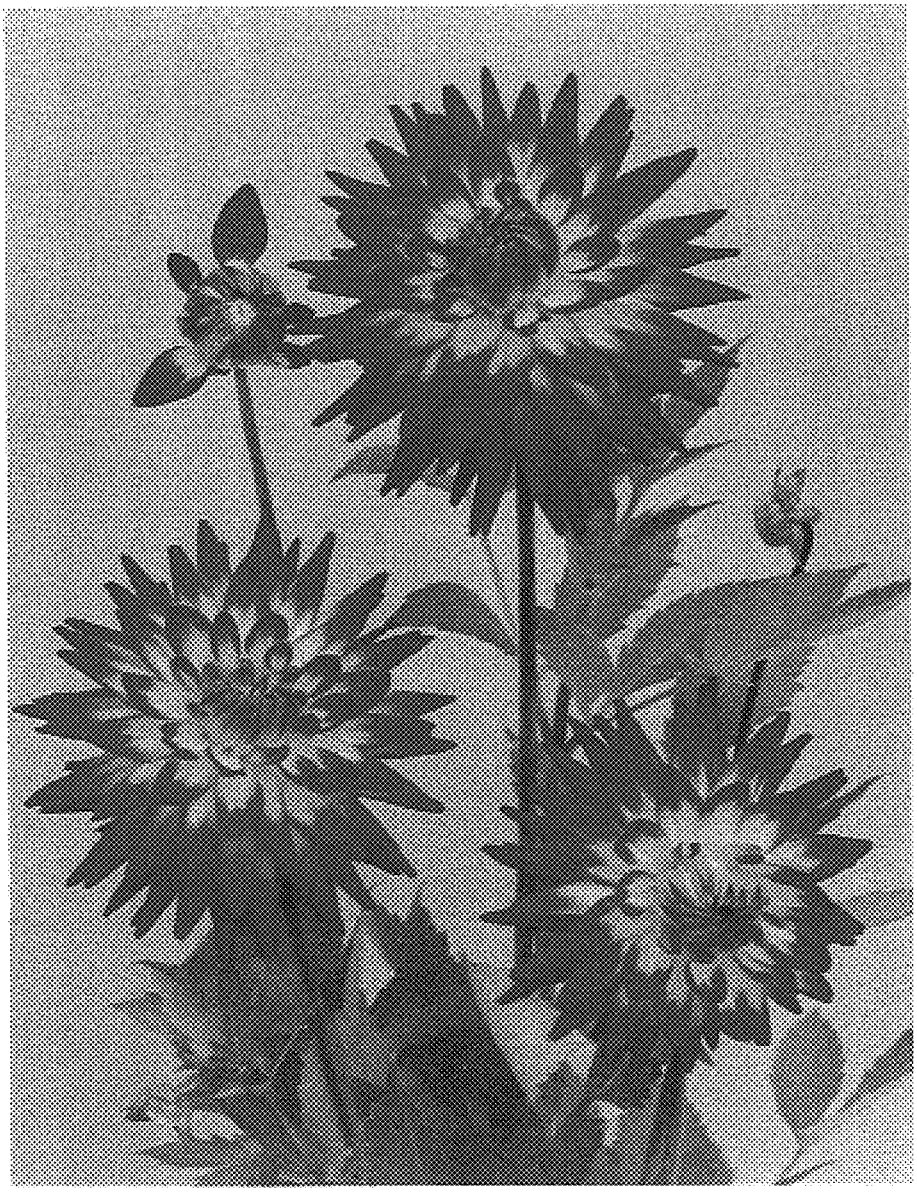

* * * * *